United States Patent [19]
Dunn et al.

[11] Patent Number: 5,648,536
[45] Date of Patent: Jul. 15, 1997

[54] PROCESS FOR PRODUCING IOVERSOL

[76] Inventors: Thomas Jeffrey Dunn, 9505 Byrnesville Rd., Cedar Hill, Mo. 63016; David H. White, 877 Gardenway Dr., Ballwin, Mo. 63011; Mills Thomas Kneller, 7314 Colgate Ave., University City, Mo. 63130; Michelle M. Jones, 16212 Copperwood La., Grover, Mo. 63040; Narciso Ocampo Doran, III, 3766 Vincentian La., Bridgeton, Mo. 63044

[21] Appl. No.: 482,380

[22] Filed: Jun. 7, 1995

[51] Int. Cl.$^6$ .................. C07C 233/65; C07C 231/02
[52] U.S. Cl. .................. 564/153; 424/9.454; 564/133
[58] Field of Search .................. 564/153, 133; 424/9.454

[56] References Cited

U.S. PATENT DOCUMENTS

| | | | |
|---|---|---|---|
| 4,396,598 | 8/1983 | Lin | 424/5 |
| 5,177,261 | 1/1993 | McCarthy et al. | 564/153 |
| 5,256,393 | 10/1993 | McCarthy et al. | 424/5 |
| 5,371,278 | 12/1994 | McCarthy et al. | 560/251 |

FOREIGN PATENT DOCUMENTS 1198739  12/1985  Canada.

*Primary Examiner*—Shailendra Kumar
*Attorney, Agent, or Firm*—Brian K. Stierwalt

[57] ABSTRACT

The present invention discloses a new process for producing ioversol (marketed as OPTIRAY®) comprising:

(a) reacting 5-amino-N,N'-bis(2,3-dihydroxypropyl)-2,4,6-triiodoisopthalamide with chloroacetyl chloride in a polar aprotic solvent, or combinations thereof, to produce N,N'-bis[2,3-di(2-chloroacetoxy)propyl]-5-(2-chloroacetamido)-2,4,6-triiodoisophthalamide;

(b) reacting the product of (a) with sodium hydroxide to produce N,N'-bis(2,3-dihydroxypropyl)-5-(2-chloroacetamido)-2,4,6-triiodoisopthalamide;

(c) reacting the product of (b) in water and sodium acetate to produce N,N'-bis(2,3-dihydroxypropyl)-5-glycolamido-2,4,6-triiodoisopthalamide; and (d) reacting the product of (c) with an alkylating agent capable of producing hydroxylhylated product in the presence of a base and water to produce ioversol.

10 Claims, No Drawings

PROCESS FOR PRODUCING IOVERSOL

FIELD OF THE INVENTION

This invention is in the field of imaging. In particular, the invention relates to X-ray imaging. And most particularly, the invention relates to a new process for obtaining ioversol.

BACKGROUND OF THE INVENTION

This invention relates to N,N'-bis(2,3-dihydroxypropyl)-5-N-(2-hydroxyethyl)glycolamido-2,4,6-triiodoisopthalamide (ioversol).

Ioversol is commonly used as an X-ray contrast agent. The agent may be used in various radiographic procedures including those involving cardiography, coronary arteriography, aortography, cerebral and peripheral angiography, arthrography, intravenous pyelography and urography as well as myelography.

The present commercial manufacture of ioversol proceeds in four steps from bis(2,3-dihydroxypropyl)-2,4,6-triiodo-5-aminoisophthalamide to crude ioversol product, which product is subsequently purified. This conversion utilizes two expensive raw materials, acetoxyacetyl chloride (AAC) and bromoethylacetate (BEA), which together contribute to greater than 25% of the final product material cost. Additionally, the present commercial manufacturing process requires the use of several expensive, environmentally undesirable and/or reactive solvents such as 1,1,2-trichloroethane (TCE), dimethylsulfoxide (DMSO) and amylacetate. Each of these solvents have been particularly troublesome in manufacturing due to difficulties in recovery and other operational difficulties. TCE, in particular, is a chlorinated solvent of considerable concern in manufacturing. Thus, there exists a need for an improved process for the manufacture of ioversol which incorporates less expensive and more environmentally suitable raw materials.

SUMMARY OF THE INVENTION

The present invention provides a new process for producing ioversol (marketed as OPTIRAY®) comprising:

(a) reacting 5-amino-N,N'-bis(2,3-dihydroxypropyl)-2,4,6-triiodoisopthalamide with chloroacetyl chloride in a polar aprotic solvent or combinations thereof to produce N,N'-bis[2,3-di(2-chloroacetoxy)propyl]-5-(2-chloroacetamido)-2,4,6-triiodoisophthalamide;

(b) reacting the product of (a) with sodium hydroxide to produce N,N'-bis(2,3-dihydroxypropyl)-5-(2-chloroacetamido)-2,4,6-triiodoisopthalamide;

(c) reacting the product of (b) in water and sodium acetate to produce N,N'-bis(2,3-dihydroxypropyl)-5-glycolamido-2,4,6-triiodoisopthalamide; and (d) reacting the product of (c) with an alkylating agent capable of producing a hydroxyethylated product in the presence of a base and water to produce ioversol.

The new synthetic route replaces the high cost AAC and BEA components with chloroacetylchloride (CAC) and an alkylating agent which is capable of producing a hydroxyethylated product, respectively, thus reducing the introduction of these components to a more elementary and far less expensive archetype. Further, except for a small quantity of the polar aprotic solvent dimethylacetamide (DMAC) utilized in the initial step, the remaining reactions are conducted in an aqueous reaction medium, eliminating TCE, DMSO and amyl acetate and their corresponding costs and environmental difficulties.

DETAILED DESCRIPTION

The current process for producing ioversol is generally depicted in Table 1.

TABLE I

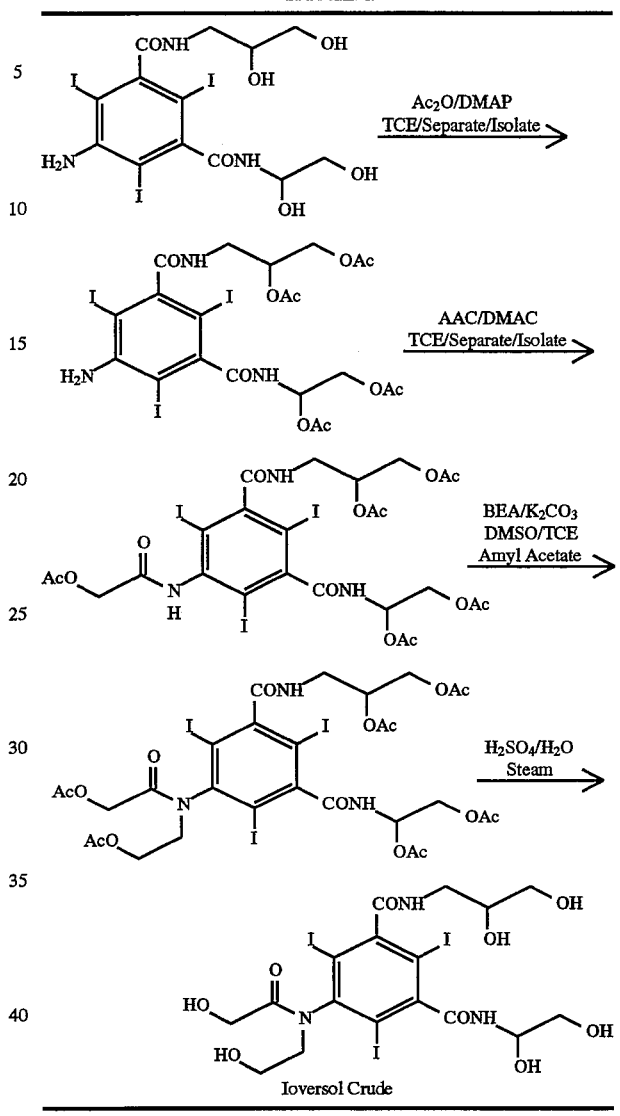

The current general procedure for producing ioversol is as follows:

STEP 1.

Preparation of 5-Amino-N,N'-bis(2,3-diacetoxypropyl)-2,4,6-triiodoisophthalamide 5-Amino-N,N'-bis(2,3-dihydroxpropyl)-2,4,6-triiodoisophthalamide is dissolved in N,N-diomethylacetamide and acetylated with acetic anhydride, using 4-dimethylaminopyridine as a catalyst, to produce 5-amino-N,N'-bis(2,3-diacetoxypropyl)-2,4,6-triiodoisophthalamide. Upon completion of the reaction, the mixture is diluted with 1,1,2-trichloroethane and washed with aqueous sodium carbonate and aqueous sodium chloride solutions to remove acetic acid, which is the by-product of the reaction. The resulting 1,1,2-trichloroethane solution of the product is used in STEP #2.

STEP 2.

Preparation of 5-Acetoxyacetamido-N,N'-bis(2,3-diacetoxypropyl)-2,4,6-triiodoisophthalamide Most of the solvent (1,1,2-trichloroethane) is distilled from the solution of 5-amino-N,N'bis(2,3-diacetoxypropyl)-2,4,6-triiodoisophthalamide prepared in STEP #1. The reaction solvent, N,N-dimethylacetamide, is added. Excess acetoxyacetyl chloride is added and the reaction mixture is stirred at ca. 40° C. until the reaction is completed. 5-Acetoxyacetamido-N,N'-bis(2,3-diacetoxypropyl)-2,4,6-triiodoisophthalamide is formed. 1,1,2-trichloroethane is added to dilute the reaction mixture and the solution is washed with aqueous sodium bicarbonate and aqueous sodium chloride solutions to remove acetoxyacetic acid and other by-products. The resulting organic layer which contains the reaction product is used in the next step.

STEP 3.

Preparation of 5-[N-(2-Acetoxyethyl)acetoxyacetamido]-N,N'-bis(2,3-diacetoxypropyl)-2,4,6-triiodoisophthalamide Solvent (1,1,2-trichloroethane) is distilled from the solution of 5-acetoxyacetamido-N,N'-bis(2,3-diacetoxypropyl)-2,4,6-triiodoisophthalamide prepared in STEP #2. Dimethyl sulfoxide is added as the reaction solvent. Potassium carbonate and 2-bromoethyl acetate are added and the mixture is stirred for ca. 10 hours at ca. 40° C. to complete the reaction to form 5-[N-(2-acetoxyethyl)acetoxyacetamido]-N,N'-bis(2,3-diacetoxypropyl)-2,4,6-triiodoisophthalamide. After the reaction is completed 1,1,2-trichloroethane is added to dilute the mixture. To remove the inorganic salts and dimethyl sulfoxide in the medium, the mixture is washed once with deionized water, and twice with aqueous sodium chloride solution. The organic layer, which contains the product, is then distilled to remove the solvent and the residue is dissolved in amyl acetate while the mixture is still hot. The mixture is then cooled and stirred continuously to complete the crystallization. The reaction product is collected and dried. After testing, it is used in STEP #4 to prepare crude ioversol aqueous solution.

STEP 4.

Preparation of N,N'-bis(2,3-dihydroxypropyl)-5-[N-(2-hydroxyethyl)qlycolamido]-2,4,6-triiodoisophthalamide, (crude ioversol aqueous solution)

5-[N-(2-Acetoxyethyl)acetoxyacetamido]-N,N'bis(2,3-diacetoxypropy)-2,4,6-triiodoisophthalamide solids are slurried in hot water containing a catalytic quantity of sulfuric acid. The solid gradually dissolves as it is heated with the steam on the jacket. The material is hydrolyzed to produce crude ioversol and acetic acid as a by-product. To remove the acetic acid, clean steam is sparged into the reactor. The solution volume is maintained constant by adding deionized water during the reaction and acetic acid removal. The reaction is tested for completeness of hydrolysis and for the removal of acetic acid.

The solution which contains ioversol, (crude ioversol aqueous solution) is cooled and utilized in subsequent purification steps.

The process of the invention for producing ioversol is depicted in Table 2.

TABLE II

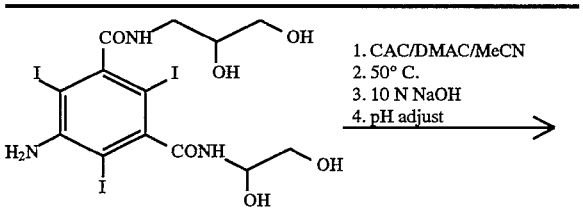

1. CAC/DMAC/MeCN
2. 50° C.
3. 10 N NaOH
4. pH adjust

TABLE II-continued

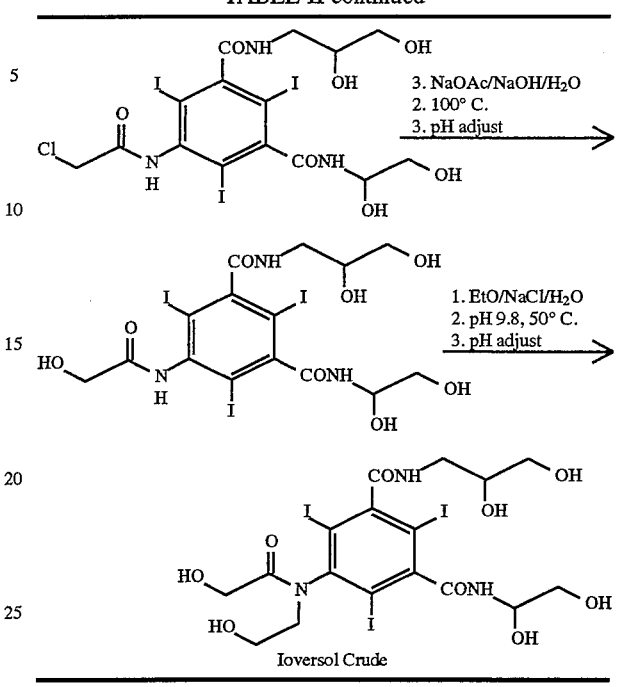

The general procedure for the process of the invention involves reacting 5-amino-N,N'-bis(2,3-dihydroxypropyl)-2,4,6-triiodoisophthalamide with chloroacetyl chloride in a polar aprotic solvent.

The resulting product is hydrolyzed with sodium hydroxide. A homogeneous solution is obtained by adding water. Precipitation is affected to yield N,N'-bis(2,3-dihydroxypropyl)-5-(2-chloroacetamido)-2,4,6-triiodoisophthalamide. This product is mixed with water and sodium acetate and the pH adjusted. A base is added as the reaction proceeds in order to maintain pH at a constant level and produce N,N'-bis(2,3-dihydroxypropyl)-5-glycolamido-2,4,6-triiodoisopthalamide. This product from the previous step is subsequently treated in aqueous solution with a base and reacted with an alkylating agent capable of producing an hydroxyethylated product. The reaction product is crude ioversol. The reaction pH is maintained by addition of mineral acid. Finally, salt and low molecular weight impurities are removed.

Polar aprotic solvents for use with the invention include dimethylacetamide, acetonitrile, dimethylsulfoxide, dimethylformamide, tetrahydrofuran, dimethoxyethane, acetonitrile, or combinations thereof. Suitable bases for use with the water include sodium hydroxide, lithium hydroxide, ammonium hydroxide, and potassium hydroxide. Alkylating agents capable of producing a hydroxyethylated product suitable for use with the invention include 2-chloroethanol, ethylene oxide, ethylene carbonate, 2-bromoethanol, 2-iodoethanol, and 2-tosylethanol.

Specifically, the process of the invention is detailed in the Examples section of this document.

The following examples illustrate the specific embodiments of the invention described in this document. As would be apparent to skilled artisans, various changes and modifications are possible and are contemplated within the scope of the invention described.

EXAMPLES

Example 1

Preparation of N,N'-bis[2,3-di(2-chloroacetoxy) propyl]-5-(2-chloroacetamido)-2,4,6-triiodoisophthalamide

5-Amino-N,N'-bis (2,3-dihydroxypropyl)-2,4,6-triiodoisophthalamide (84.6 g, 0.12 moles) was dissolved in 172 mL of N,N-dimethylacetamide at 50° C. The solution was cooled to 10° C. and 62 mL (88.09g, 0.78 moles) of chloroacetyl chloride were added over 30 minutes. The reaction mixture was stirred for 3 hours at 50° C. HPLC analysis of the reaction mixture showed that it contained 99.8% N,N'-bis[2,3-di-(2-chloroacetoxy)propyl]-5-(2-chloroacetamido)-2,4,6-triiodo-isophthalamide. The material was carried forward to Example 2 without further purification.

Example 2

Preparation of N,N'-bis(2,3-dihydroxypropyl)-5-(2-chloroacetamido)-2,4,6-triiodoisophthalamide

N,N'-bis[2,3-di(2-chloroacetoxy)propyl]-5-(2-chloroacetamido)-2,4,6-triiodoisophthalamide in N,N-dimethylacetamide, from Example 1, was hydrolyzed by adding 156 mL of 10N sodium hydroxide solution (1.56 moles). Water (100 mL) was then added to the mixture to give a homogeneous solution. 1N Hydrochloric acid (59 mL, 0.59 moles) was added to precipitate the N,N'-bis (2,3-dihydroxypropyl)-5-(2-chloroacetamido)-2,4,6-triiodoisophthalamide. The precipitate was collected and washed with water. The wet product was dried at 60° C. in a vacuum oven to give 81.69 g of product, 88.4% yield. The material was 100 % pure by HPLC analysis.

Example 3

Preparation of N,N'-bis[2,3-di(2-chloroacetoxy) propyl]-5-(2-chloroacetamido)-2,4,6-triiodoisophthalamide

5-Amino-N,N'-bis(2,3-dihydroxypropyl)-2,4,6-triiodoisophthalamide (70.5 g, 0.1 moles) was dissolved in 71 mL of N,N-dimethylacetamide at 50° C. Acetonitrile (71 mL) was added to the mixture. Chloroacetyl chloride (52 mL, 73.4 g, 0.65 moles) was added over 30 minutes. The reaction mixture was stirred for 3 hours at 50° C. HPLC analysis of the reaction mixture showed that it contained 98.5% N,N'-bis[2,3-di(2-chloroacetoxy)propyl]-5-(2-chloroacetamido)-2,4,6-triiodoisophthalamide. The material was carried forward to Example 4, without further purification.

Example 4

Preparation of N,N'-bis(2,3-dihydroxypropyl)-5-(2-chloroacetamido)-2,4,6-triiodoisophthalamide

N,N'-bis[2,3-di(2-chloroacetoxy)propyl]-5-(2-chloroacetamido)-2,4,6-triiodoisophthalamide in N,N-dimethylacetamide and acetonitrile, from Example 3, was hydrolyzed by adding 130 mL of 10N sodium hydroxide solution (1.3 moles). Water (36 mL) was then added to the mixture to give a homogeneous solution. 1N Hydrochloric acid (100 mL, 0.1 moles) was added to precipitate the N,N'-bis(2,3-dihydroxypropyl)-5-(2-chloroacetamido)-2,4,6-triiodoisophthalamide. The precipitate was collected and washed with water. The wet product was dried at 60° C. in a vacuum oven to give 71.6 g of product, 92.2% yield. The material was 100% pure by HPLC analysis.

Example 5

Preparation of N,N'-bis(2,3-dihydroxypropyl)-5-glycolamido-2,4,6-triiodoisophtha lamide

N,N'-bis(2,3-dihydroxypropyl)-5-(2-chloroacetamido)-2,4,6-triiodo isophthalamide (39.08 g, 0.05 moles) was suspended in 150 mL of water. Sodium acetate (32.8 g, 0.4 moles) was added and the pH of the mixture was adjusted to 6.4 with 1 mL of 12N hydrochloric acid. The mixture was heated to reflux. The pH of the reaction mixture was maintained at 6.3 to 6.5 by adding 5N sodium hydroxide solution. At the end of the reaction the mixture contained 96.4% N,N'-bis(2,3-dihydroxypropyl)-5-glycolamido-2,4,6-triiodoisophtha lamide. The reaction mixture was cooled to room temperature and the product precipitated from the reaction mixture. The precipitate was isolated and washed with water. The solid was dried at 60° C. in a vacuum oven to give 33 g of product, 94% yield. The material was 97.75% pure by HPLC analysis.

Example 6

Preparation of N,N'-bis(2,3-dihydroxypropyl)-5-N-(2-hydroxyethyl)glycolamido-2,4,6-triiodoisophthalamide

N,N'-bis(2,3-dihydroxypropyl)-5-glycolamido-2,4,6-triiodoisophtha lamide (30.0g, 0.039 moles), aqueous sodium hydroxide (50% w/w solution; 7.28 g, 0.091 moles), and deionized water (85 mL) were combined in a 500 mL, 3-necked round bottomed flask equipped with thermometer, overhead stirrer, and a reflux condenser connected to a 10% aqueous sodium hydroxide trap. The mixture was heated to 50° C., and the 2-chloroethanol was added all at once by syringe. Heating was continued for 7 hours. The mixture was cooled to 10°–15° C., and the reaction was quenched with 5 mL of concentrated hydrochloric acid. By HPLC the reaction mixture contained 93% N,N'-bis(2,3-dihydroxypropyl)-5-N-(2-hydroxyethyl)glycolamido-2,4,6-triiodoisophthalamide. The reaction mixture was carried forward without further processing.

Example 7

Preparation of N,N'-bis(2,3-dihydroxypropyl)-5-N-(2-hydroxyethyl)glycolamido-2,4,6-triiodoisophthalamide

N,N'-bis(2,3-dihydroxypropyl)-5-glycolamido-2,4,6-triiodoisophtha lamide (17.65 g, 0.023 moles), NaCl (1.3 g, 0.023 moles), NaOAc (15.1 g, 0,184 moles), and deionized water (165 mL) were combined in a 500 mL 4-necked round bottomed flask equipped with thermometer, overhead stirrer, air-cooled reflux condenser, and a glass tube attached to an ethylene oxide gas cylinder. The mixture was cooled to 2° C. with an ice bath, and ethylene oxide (18.11 g, 0.411 moles) was bubbled subsurface at a rate of ca. 190 mL/min. The air-cooled condenser and ethylene oxide inlet tube were removed and replaced with a dry ice condenser attached to a 10% aqueous NaOH trap. The mixture was heated to 50° C. The pH was maintained at 10.0 with 1N hydrochloric acid while the mixture was heterogeneous. When the solids dissolved, the pH was maintained at 9.6–9.8. After 4 hours, the mixture was cooled to room temperature and quenched first with 1.0N hydrochloric acid (40 mL) and then with concentrated hydrochloric acid (20 mL) to pH 4.5. The reaction mixture contained 93% ioversol by HPLC. Assay of the product gave a yield of 17.6 g (94.3%). The reaction mixture was carried forward without further processing.

Example 8

Removal of salts and other lower molecular weigh impurities from crude ioversol

A column (2.5 cm diameter, 29 cm height) was packed, using the procedure recommended by the manufacturer, with Amberlite XAD-16 resin. Crude ioversol (4.5 g) containing ioversol (45.3%), sodium acetate (40.9%), NaCl (3.2%), ethylene glycol (10.2%) and other organic impurities was dissolved in water (12 mL) and loaded into the XAD-16 column. The column was eluted with water at a flow rate of 3.0 mL per minute. The elution profile was monitored with a conductivity meter for ionic substances and an UV detector at 254 nm for ioversol. When the conductivity started to increase, fractions were collected (30 mL each). The salts and other lower molecular weight impurities were eluted from the column. The column was then eluted with a mixture of methanol and water (50/50) which cleanly effected deadsorption of ioversol from the column in 95–99% yield. The XAD-16 column may be re-equilibrated with water for reuse. The isolated ioversol fraction contained less than 5 ppm of ethylene glycol (by HPLC) and were devoid of ionic impurities (by conductivity analyses).

Although the invention has been described with respect to specific modifications, the details thereof are not to be construed as limitations, for it will be apparent that various equivalents, changes and modifications may be resorted to without departing from the spirit and scope thereof, and it is understood that such equivalent embodiments are to be included therein.

What is claimed is:

1. A process for producing ioversol comprising:
    (a) reacting 5-amino-N,N'-bis(2,3-dihydroxypropyl)-2,4,6-triiodoisopthalamide with chloroacetyl chloride in a polar aprotic solvent, or combinations thereof, to produce N,N'-bis[2,3-di(2-chloroacetoxy)propyl]-5-(2-chloroacetamido-2,4,6-triiodoisophthalamide;
    (b) reacting the product of (a) with sodium hydroxide to produce N,N'-bis(2,3-dihydroxypropyl)-5-(2-chloroacetamido)-2,4,6-triiodoisopthalamide;
    (c) reacting the product of (b) in water and sodium acetate to produce N,N'-bis(2,3-dihydroxypropyl)-5-glycolamido-2,4,6-triiodoisopthalamide; and
    (d) reacting the product of (c) with an alkylating agent capable of producing a hydroxyethylated product in the presence of a base and water to produce ioversol.

2. The process of claim 1 wherein the polar aprotic solvent is selected from dimethylacetamide, acetonitrile, dimethylsulfoxide, dimethylformamide, tetrahydrofuran, dimethoxyethane, acetonitrile, or mixtures thereof.

3. The process of claim 2 wherein the polar aprotic solvent is N,N-dimethylacetamide.

4. The process of claim 2 wherein the polar aprotic solvent is N,N-dimethylacetamide and acetonitrile.

5. The process of claim 1 wherein the alkylating agent in (d) is selected from the group consisting of 2-chloroethanol, ethylene oxide, ethylene carbonate, 2-bromoethanol, 2-iodoethanol and 2-tosylethanol.

6. The process of claim 5 wherein the alkylating agent is ethylene oxide.

7. The process of claim 1 wherein the base in (d) is selected from sodium hydroxide, lithium hydroxide, ammonium hydroxide and potassium hydroxide.

8. The process of claim 7 wherein the base is sodium hydroxide.

9. A process for producing ioversol comprising:
    (a) reacting 5-amino-N,N'-bis(2,3-dihydroxypropyl)-2,4,6-triiodoisopthalamide with chloroacetyl chloride in N,N-dimethylacetamide to produce N,N'-bis[2,3-di(2-chloroacetoxy)propyl]-5-(2-chloroacetamido)-2,4,6-triiodoisophthalamide;
    (b) reacting the product of (a) with sodium hydroxide to produce N,N'-bis(2,3-dihydroxypropyl)-5-(2-chloroacetamido)-2,4,6-triiodoisopthalamide;
    (c) reacting the product of (b) in water and sodium acetate to produce N,N'-bis(2,3-dihydroxypropyl)-5-glycolamido-2,4,6-triiodoisopthalamide; and
    (d) reacting the product of (c) with sodium hydroxide, water, and ethylene oxide, to produce ioversol.

10. A process for producing ioversol comprising:
    (a) reacting 5-amino-N,N'-bis(2,3-dihydroxypropyl)-2,4,6-triiodoisopthalamide with chloroacetyl chloride in N,N-dimethylacetamide and acetonitrile, to produce N,N'-bis[2,3-di(2-chloroacetoxy)propyl]-5-(2-chloroacetamido)-2,4,6-triiodoisophthalamide;
    (b) reacting the product of (a) with sodium hydroxide to produce N,N'-bis(2,3-dihydroxypropyl)-5-(2-chloroacetamido)-2,4,6-triiodoisopthalamide;
    (c) reacting the product of (b) in water and sodium acetate to produce N,N'-bis(2,3-dihydroxypropyl)-5-glycolamido-2,4,6-triiodoisopthalamide; and
    (d) reacting the product of (c) with sodium hydroxide, water, and ethylene oxide, to produce ioversol.

* * * * *